United States Patent
Pei et al.

(10) Patent No.: US 10,434,315 B2
(45) Date of Patent: Oct. 8, 2019

(54) SYSTEMS AND METHODS FOR AUTOMATICALLY DETERMINING PACE AND SENSE CONFIGURATIONS FOR AN IMPLANTABLE DEVICE

(71) Applicant: PACESETTER, INC., Sylmar, CA (US)

(72) Inventors: Xing Pei, Thousand Oaks, CA (US); James Chien, Arcadia, CA (US)

(73) Assignee: Pacesetter, Inc., Sylmar, CA (US)

( * ) Notice: Subject to any disclaimer, the term of this patent is extended or adjusted under 35 U.S.C. 154(b) by 12 days.

(21) Appl. No.: 15/295,816

(22) Filed: Oct. 17, 2016

(65) Prior Publication Data

US 2017/0128730 A1    May 11, 2017

Related U.S. Application Data

(60) Provisional application No. 62/244,074, filed on Oct. 20, 2015.

(51) Int. Cl.
| | |
|---|---|
| *A61N 1/365* | (2006.01) |
| *A61N 1/368* | (2006.01) |
| *A61N 1/372* | (2006.01) |
| *A61N 1/39* | (2006.01) |

(52) U.S. Cl.
CPC ....... *A61N 1/36521* (2013.01); *A61N 1/3684* (2013.01); *A61N 1/37235* (2013.01); *A61N 1/3962* (2013.01)

(58) Field of Classification Search
CPC ............ A61N 1/36521; A61N 1/36571; A61N 2001/083; A61N 1/3614
See application file for complete search history.

(56) References Cited

U.S. PATENT DOCUMENTS

| | | | |
|---|---|---|---|
| 6,754,530 B2 * | 6/2004 | Bakels ................ | A61N 1/3622 607/14 |
| 7,020,523 B1 * | 3/2006 | Lu ...................... | A61N 1/36185 607/27 |

* cited by examiner

*Primary Examiner* — Alyssa M Alter

(57) ABSTRACT

The present disclosure provides systems and methods for automatically determining pace and sense configurations for an implantable cardiac device. A method of operating an implantable cardiac device includes automatically determining, during a detection phase, a pace and sense configuration for the implantable cardiac device based on a plurality of first impedance measurements. The method further includes confirming, during a confirmation phase, the pace and sense configuration based on a plurality of second impedance measurements, and operating the implantable cardiac device in accordance with the pace and sense configuration.

20 Claims, 11 Drawing Sheets

SYSTEMS AND METHODS FOR AUTOMATICALLY DETERMINING PACE AND SENSE CONFIGURATIONS FOR AN IMPLANTABLE DEVICE

This application claims the benefit of U.S. Provision Patent Application Ser. No. 62/244,074, filed Oct. 20, 2015, entitled "SYSTEMS AND METHODS FOR AUTOMATICALLY DETERMINING PACE AND SENSE CONFIGURATIONS FOR AN IMPLANTABLE DEVICE," which is incorporated herein by reference.

FIELD OF THE DISCLOSURE

The present disclosure relates generally to cardiac stimulation systems, and more particularly to automatically determining pace and sense configurations for an implantable cardiac device.

BACKGROUND ART

Numerous implantable medical devices exist today that implement a variety of detection schemes and therapies to address various cardiac arrhythmias while supporting heart function to facilitate adequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all cardiac patients suffer debilitating symptoms immediately. Some may live actively for years. Yet, with few exceptions, the disease is relentlessly progressive. As cardiac disease progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for cardiac diseases is typically centered around treatment with medicine. Cardiac surgery has also been performed on a small percentage of patients with particular etiologies. Although advances in pharmacological therapy have significantly improved the survival rate and quality of life of patients, some cardiac patients are refractory to drug therapy, have a poor prognosis and limited exercise tolerance. In recent years, implantable cardiac devices, such as pacemakers and implantable cardioverter defibrillators (ICDs) have emerged as effective treatments for many patients with drug-refractory cardiac disease.

For implantable device systems, safety and ease of operation are important. In at least some known systems, a user (e.g., a physician) must program, into the implantable device prior to or during implantation, lead configurations for the implantable device based on the type of lead implanted. Further, nearly all modern cardiac implantable systems that support pacing require an external instrument a programmer) to perform the programming. Accordingly, it would be desirable to have an implantable device that is able to automatically determine pace and sense configurations to provide cardiac support to the patient with or without pre-programming, improving flexibility for the system and reducing time required for the implantation procedure.

BRIEF SUMMARY OF THE DISCLOSURE

In one embodiment, the present disclosure is directed to an implantable cardiac device. The implantable cardiac device includes at least one lead configured to perform pacing and sensing operations, an impedance sensor, a memory, and a controller communicatively coupled to the memory and configured to automatically determine, during a detection phase, a pace and sense configuration for the at least one lead based on a plurality of first impedance measurements acquired using the impedance sensor, and confirm, during a confirmation phase, the pace and sense configuration based on a plurality of second impedance measurements acquired using the impedance sensor.

In another embodiment, the present disclosure is directed to a system. The system includes an implantable cardiac device including at least one lead configured to perform pacing and sensing operations, an impedance sensor, a memory, and a controller communicatively coupled to the memory and configured to automatically determine, during a detection phase, a pace and sense configuration for the at least one lead based on a plurality of first impedance measurements acquired using the impedance sensor, and confirm, during a confirmation phase, the pace and sense configuration based on a plurality of second impedance measurements acquired using the impedance sensor. The system further includes a programmer communicatively coupled to the implantable cardiac device.

In another embodiment, the present disclosure is directed to a method of operating an implantable cardiac device. The method includes automatically determining, during a detection phase, a pace and sense configuration for the implantable cardiac device based on a plurality of first impedance measurements. The method further includes restarting detection or confirming, during a confirmation phase, the pace and sense configuration based on a plurality of second impedance measurements, and operating the implantable cardiac device in accordance with the pace and sense configuration.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for automatically determining pace and sense configurations for an implantable cardiac device. A method of operating an implantable cardiac device includes automatically determining, during a detection phase, a pace and sense configuration for the implantable cardiac device based on a plurality of first impedance measurements. The method further includes confirming, during a confirmation phase, the pace and sense configuration based on a plurality of second impedance measurements, and operating the implantable cardiac device in accordance with the pace and sense configuration.

The embodiments described herein achieve automatically determining pace and sense configurations of an implanted device system (including leads) by the implantable cardiac device itself. The implantable cardiac device may include a shipped configuration (e.g., a bi-polar configuration) that provides pacing and sensing. However, as described herein, the implantable cardiac device continuously monitors whether the device has been implanted by using an impedance block to measure an unipolar lead impedance. An unipolar lead impedance below a predetermined threshold indicates that the device has contacted patient tissue.

The device then determines the type of lead implanted (i.e., bipolar or unipolar) by checking a bipolar lead impedance. If the bipolar lead impedance is below a predetermined threshold, that indicates the lead is a bipolar lead (i.e., a lead having two electrodes). The device then self-sets a corresponding pace and sense configuration, while continuously monitoring the unipolar and bipolar lead impedances until they reach a steady state, such that the lead type can be confirmed and/or adjusted accordingly. To ensure synchronization, once the pace and sense configuration is confirmed, the device communicates the pace and sense configuration to an external programmer if the device detects the presence of the external programmer.

Further, the user may selectively enable and disable the auto-detection functionality, and may also override the pace and sense configuration determined by the device. The device may also collect diagnostic data, including a date and time of implantation, measured impedances, and/or determined lead configurations.

Figure 1A:
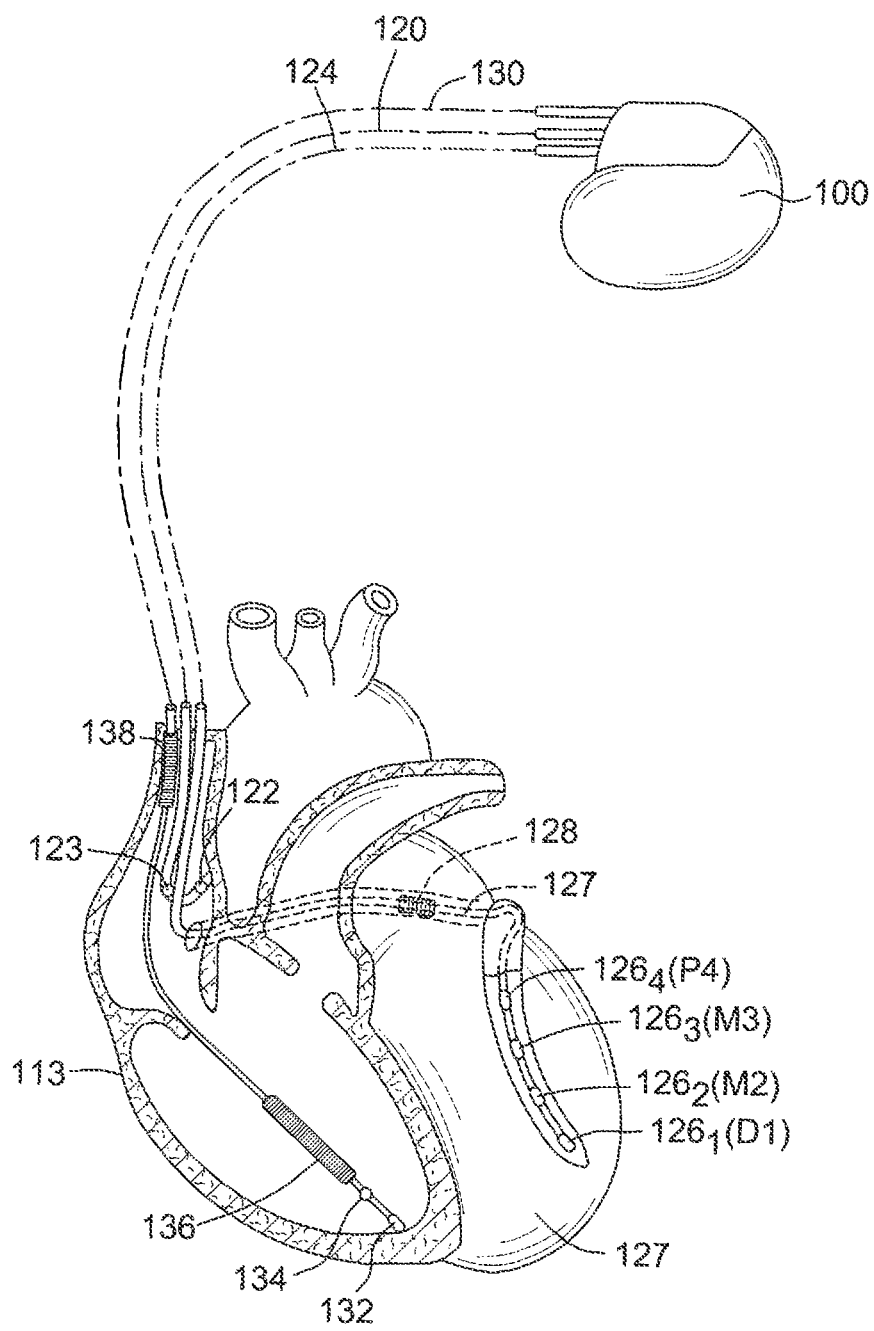
FIG. 1A is a simplified, partly cutaway view illustrating an implantable stimulation device in electrical communication with three leads implanted into a patient's heart for delivering multi-chamber stimulation and shock therapy and sensing cardiac activity.
Figure 1B:
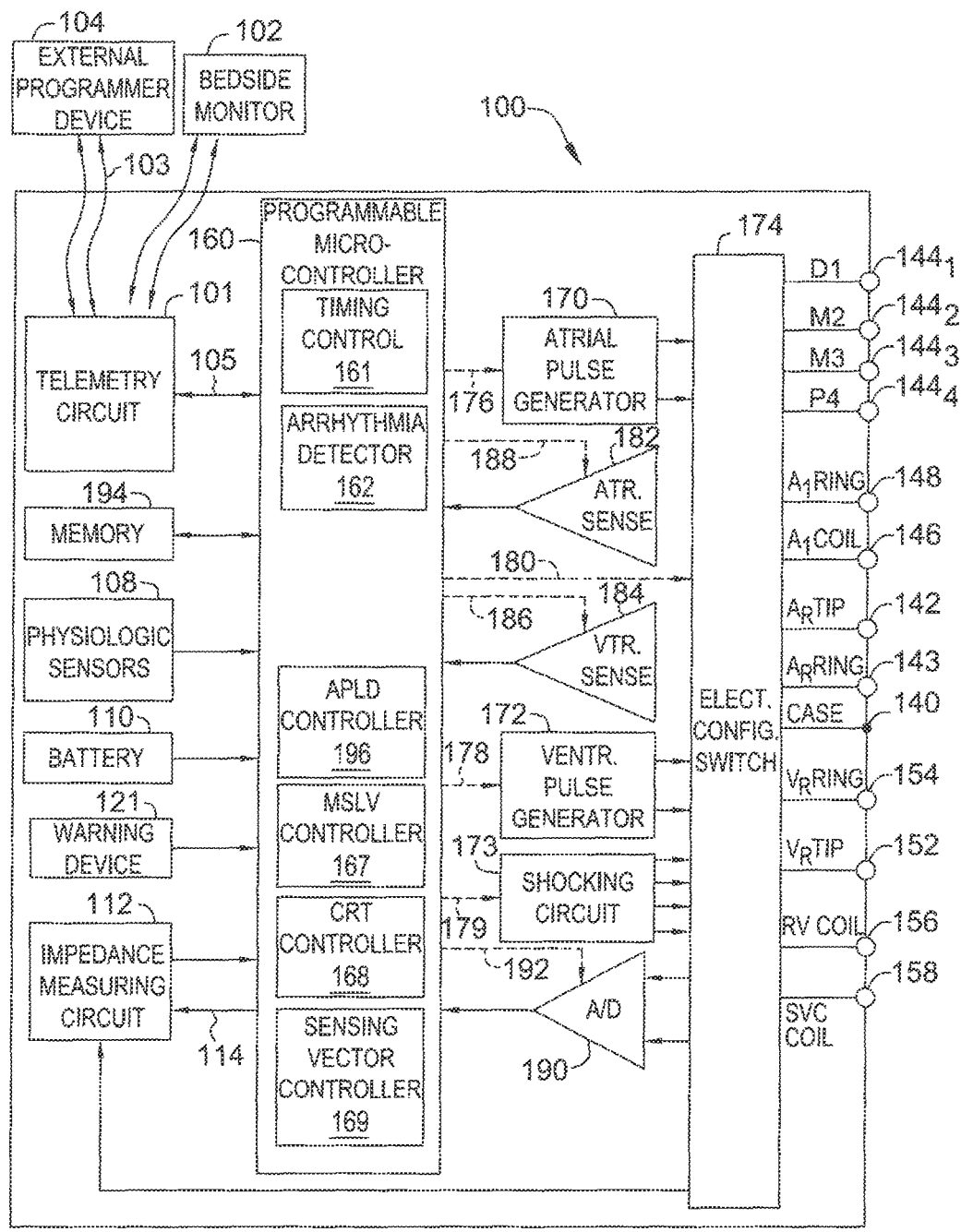
FIG. 1B is a functional block diagram of the multi-chamber implantable stimulation device of FIG. 1A, illustrating the basic elements that provide pacing stimulation, cardioversion, and defibrillation in four chambers of the heart.

With reference to FIGS. 1A and 1B, a description of an example pacemaker/implantable cardioverter-defibrillator (ICD) (i.e., and implantable cardiac device) 100 will now be provided. FIG. 1A is a simplified block diagram of pacemaker/ICD 100, which is a dual-chamber stimulation device capable of treating both fast and slow arrhythmias with stimulation therapy, including cardioversion, defibrillation, and pacing stimulation, including multi-site left ventricular (MSLV) pacing. To provide atrial chamber pacing stimulation and sensing, pacemaker/ICD 100 is shown in electrical communication with a heart 113 by way of a right atrial (RA) lead 120 having an atrial tip electrode 122 and an atrial ring electrode 123 implanted in the atrial appendage. Pacemaker/ICD 100 is also in electrical communication with heart 113 by way of a right ventricular (RV) lead 130 having, in this embodiment, a ventricular tip electrode 132, a RV ring electrode 134, a RV coil electrode 136, and a superior vena cava (SVC) coil electrode 138. Typically, RV lead 130 is transvenously inserted into the heart so as to place RV coil electrode 136 in the RV apex, and SVC coil electrode 138 in the superior vena cava. Accordingly, RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, pacemaker/ICD 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. Accordingly, an example LV lead 124 is designed to receive atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least a LA coil electrode 128. In some embodiments, LV lead 124 includes LV electrodes $126_1$, $126_2$, $126_3$, and $126_4$, but does not include LA ring and coil electrodes 127 and 128. Such a lead can be, e.g., the Quartet™ left ventricular pacing lead developed by St. Jude Medical Inc, (headquartered in St. Paul, Minn.), which includes four pacing electrodes on the left ventricular lead— enabling up to ten pacing configurations.

LV electrode $126_1$ is shown as being the most "distal" LV electrode (with relation to how far the electrode is from where LV lead 124 connects to pacemaker/ICD 100). For example, LV electrode $126_1$ may be located at the apex of the left ventricle. LV electrode $126_4$ is shown as being the most "proximal" LV electrode. For example LV electrode $126_4$ may be located at the base of the left ventricle. LV electrodes $126_2$ and $126_3$ are shown as being "middle" LV electrodes, between distal and proximal LV electrodes $126_1$ and $126_4$. Accordingly, the four LV electrodes $126_1$, $126_2$, $126_3$, and $126_4$ can be referred to respectively as electrodes D1, M2, M3 and P4 (where "D" stands for "distal", "M" stands for "middle", and "P" stands from "proximal", and the numbers are arranged from most distal to most proximal). It is also possible that more or fewer LV electrodes are provided.

Although only three leads are shown in FIG. 1A, it should also be understood that additional leads (with one or more pacing, sensing and/or shocking electrodes) might be used and/or additional electrodes might be provided on the leads already shown, such as additional electrodes on the RV or LV lead. It is also possible that less than three leads be used.

A simplified block diagram of internal components of pacemaker/ICD 100 is shown in FIG. 1B. While a particular pacemaker/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. A housing 140 for pacemaker/ICD 100, shown schematically in FIG. 1B, is often referred to as the "can", "case" or "case electrode" and may be programmably selected to act as the return electrode for all "unipolar" modes. Housing 140 may further be used as a return electrode alone or in combination with one or more of coil electrodes, 128, 136 and 138 for shocking purposes. Housing 140 further includes a connector (not shown) having a plurality of terminals. 142, 143, $144_1$-$144_4$, 146, 148, 152, 154, 156 and 158 (shown schematically and, for convenience, the names of the electrodes to which they are connected are shown next to the terminals). As such, to achieve RA sensing and pacing, the connector includes at least an RA tip terminal ($A_R$ TIP) 142 adapted for connection to the atrial tip electrode 122 and an RA ring ($A_R$ RING) electrode 143 adapted for connection to RA ring electrode 123. To achieve left chamber sensing, pacing and shocking, the connector includes an LV tip terminal $144_1$ adapted for connection to the D1 electrode and additional LV electrode terminals $144_2$, $144_3$ and $144_4$ terminals adapted for connection to the M2, M3 and P4 electrodes of quadra-pole LV lead 124.

The connector also includes an LA ring terminal ($A_L$ RING) 146 and an LA shocking terminal ($A_L$ COIL) 148, which are adapted for connection to LA ring electrode 127 and the LA coil ($A_L$ COIL) electrode 128, respectively. To support right chamber sensing, pacing and shocking, the connector further includes an RV tip terminal ($V_R$ TIP) 152, an RV ring terminal ($V_R$ RING) 154, an RV shocking terminal ($V_R$ COIL) 156, and an SVC shocking terminal (SVC COIL) 158, which are adapted for connection to RV tip electrode 132, RV ring electrode 134, RV coil electrode 136, and SVC coil electrode 138, respectively.

At the core of pacemaker/ICD 100 is a programmable microcontroller 160, which controls the various modes of stimulation therapy. As is well known in the art, microcontroller 160 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 160 includes the ability to process or monitor input signals (data) as controlled by a program code stored in a designated block of memory.

As shown in FIG. 1B, an atrial pulse generator 170 and a ventricular pulse generator 172 generate pacing stimulation pulses for delivery by RA lead 120, RV lead 130, and/or LV lead 124 via an electrode configuration switch 174. Microcontroller 160 further includes an arrhythmia detector 162 that can be utilized by the stimulation device 100 for determining desirable times to administer various therapies. Additional components of the microcontroller include a MSLV controller 167 to control the actual delivery of MSLV pacing and a cardiac resynchronization therapy (CRT) controller 168 to control CRT, which can be performed in conjunction with MSLV pacing.

Microcontroller 160 is also shown as including a sensing vector controller 169 that can be used, e.g., to control the electrode configuration switch 174 (e.g., via control signals 180) to selectively connect specific electrode(s) to sensing circuits 182 or 184 as a cathode or an anode.

Depending upon the implementation, the various components of the microcontroller may be implemented as separate software modules or the modules may be combined to permit a single module to perform multiple functions. For example, the MSLV controller and the CRT controller 168 can be combined. In addition, although shown as being components of the microcontroller, some or all of these components may be implemented separately from the microcontroller, using application specific integrated circuits (ASICs) or the like.

Switch 174 includes a plurality of switches for connecting the desired electrodes to the appropriate I/O circuits, thereby providing complete electrode programmability. Accordingly, switch 174, in response to a control signal 180 from microcontroller 160, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 182 and ventricular sensing circuits 184 may also be selectively coupled to RA lead 120, LV lead 124, and RV lead 130, through switch 174 for detecting the presence of cardiac activity in each of the four chambers of the heart. Accordingly, the atrial (ATR. SENSE) and ventricular (VTR. SENSE) sensing circuits, 182 and 184, may include dedicated sense amplifiers, multiplexed amplifiers or shared amplifiers. Switch 174 determines the "sensing polarity" of the cardiac signal by selectively closing the appropriate switches, as is also known in the art. In this way, a clinician may program the sensing polarity independent of the stimulation polarity. Each sensing circuit, 182 and 184, preferably employs one or more low power, precision amplifiers with programmable gain and/or automatic gain control, bandpass filtering, and a threshold detection circuit, as known in the art, to selectively sense the cardiac signal of interest. The automatic gain control enables pacemaker/ICD 100 to deal effectively with the difficult problem of sensing the low amplitude signal characteristics of atrial or ventricular fibrillation. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are applied to the inputs of an analog-to-digital (A/D) data acquisition system 190. Data acquisition system 190 is configured to acquire intracardiac electrogram signals, convert the raw analog data into a digital signal, and store the digital signals for later processing and/or telemetric transmission to an external programmer 104 or a bedside monitor or personal advisory module (PAM) 102. Data acquisition system 190 is coupled to RA lead 120, LV lead 124, and RV lead 130 through switch 174 to sample cardiac signals across any pair of desired electrodes. Microcontroller 160 is further coupled to a memory 194 by a suitable data/address bus, wherein the programmable operating parameters used by microcontroller 160 are stored and modified, as required, in order to customize the operation of pacemaker/ICD 100 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of implantable pacemaker/ICD 100 may be non-invasively programmed into memory 194 through a telemetry circuit 101 in telemetric communication with external device 104 or bedside monitor 102, such as a programmer, transtelephonic transceiver, or a diagnostic system analyzer. The telemetry circuit 101 is activated by the microcontroller by a control signal 106. Telemetry circuit 101 advantageously allows intracardiac electrograms and status information relating to the operation of pacemaker/ICD 100 (as contained in microcontroller 160 or memory 194) to be sent to external device 104 and/or bedside monitor 102 through an established communication link 103. An internal warning device 121 (also referred to as a patient alert) may be provided for generating perceptible warning signals to the patient via vibration, voltage or other methods.

Pacemaker/ICD 100 further includes an accelerometer or other physiologic sensor 108, commonly referred to as a "rate-responsive" sensor because it is typically used to adjust pacing stimulation rate according to the exercise state of the patient. Pacemaker/ICU additionally includes a battery 110 that provides operating power to the circuits shown in FIG. 1B. As further shown in FIG. 1B, pacemaker/ICD 100 is shown as having an impedance measuring circuit 112, which is enabled by the microcontroller 160 via a control signal 114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. Impedance measuring circuit 112 is advantageously coupled to switch 174 so that any desired electrode may be used.

In the case where pacemaker/ICD 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, microcontroller 160 further controls a shocking circuit 173 by way of a control signal 179. Shocking circuit 173 generates shocking pulses of low (up to 0.1 joules), moderate (0.1-10 joules) or high energy (11 to 40 joules or more), as controlled by the microcontroller 160. Such shocking pulses are applied to the heart of the patient through at least two shocking electrodes, and as shown in this embodiment, selected from LA coil electrode 128, RV coil electrode 136, and/or SVC coil electrode 138. Housing 140 may act as an active electrode in combination with RV electrode 136, or as part of a split electrical vector using SVC coil electrode 138 or LA coil electrode 128 using RV electrode 136 as a common electrode).

In this embodiment, microcontroller further includes an automatic lead polarity detection (ALPD) controller 196. ALPD controller 196 automatically determines a pace and sense configuration for pacemaker/ICD 100, as described in more detail below.

Pacemaker/ICD 100 is provided as an example. One or ordinary skill in the art would understand that embodiments described herein can be used with alternative types of implantable devices. Accordingly, embodiments described herein should not be limited to use only with the above described device.

Figure 2:
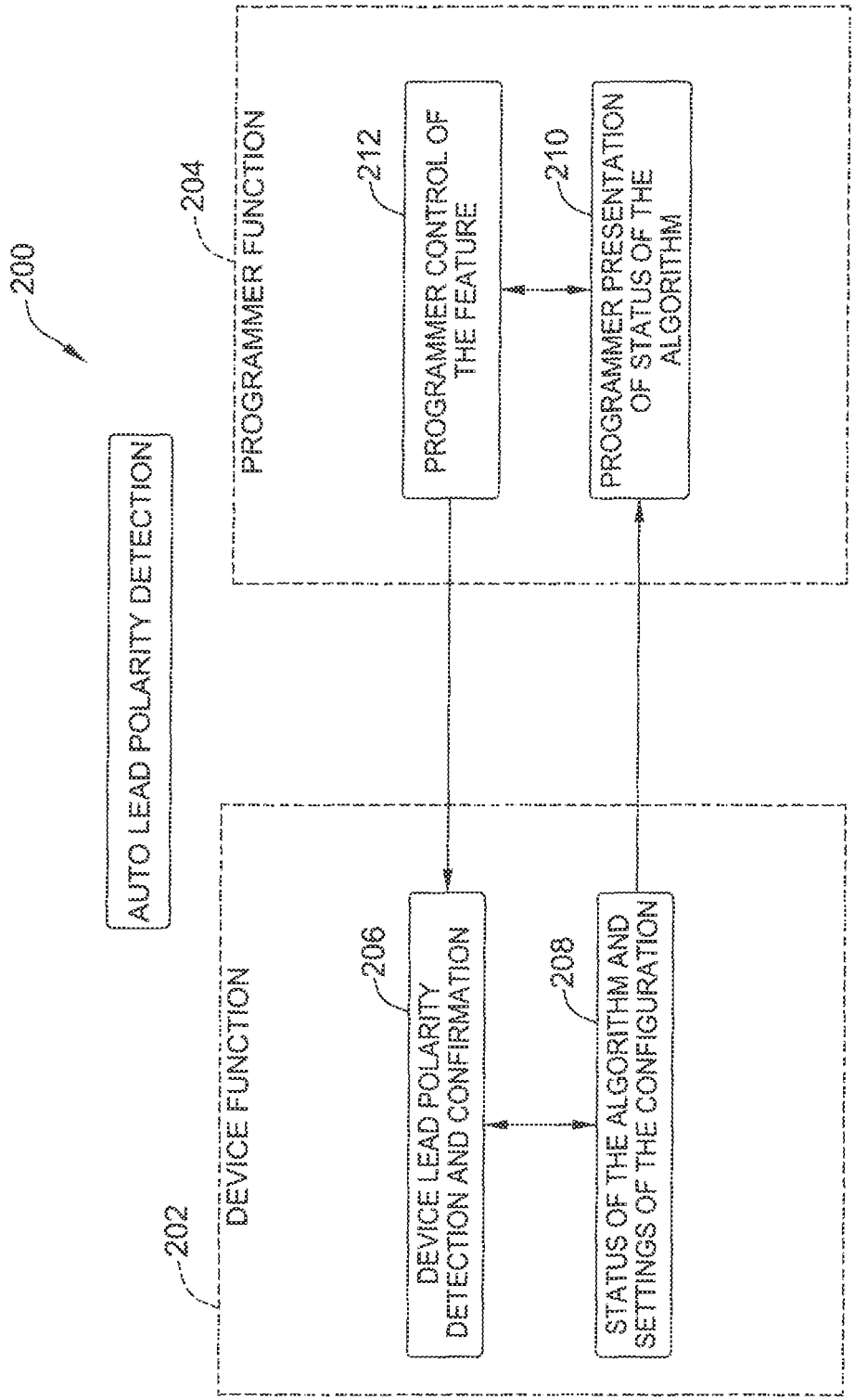
FIG. 2 is a high-level functional diagram of automatic lead polarity detection (ALPD) system.

FIG. 2 is a high-level functional diagram of an ALPD system 200. In this embodiment, ALPD system 200 includes a device 202, such as pacemaker/ICD 100 (shown in FIGS. 1A and 1B), and a programmer 204, such as external device 104 (shown in FIG. 1B). As shown in FIG. 2, at block 206, device 202 performs a device lead polarity detection and confirmation algorithm. At block 208, device 202 determines a status of the algorithm and settings of the configuration determined by the algorithm. This information is communicated and presented to external programmer 204 at block 210. At block 212, programmer 204 communicates with and controls device 202 based on the received information and user input.

Figure 3:
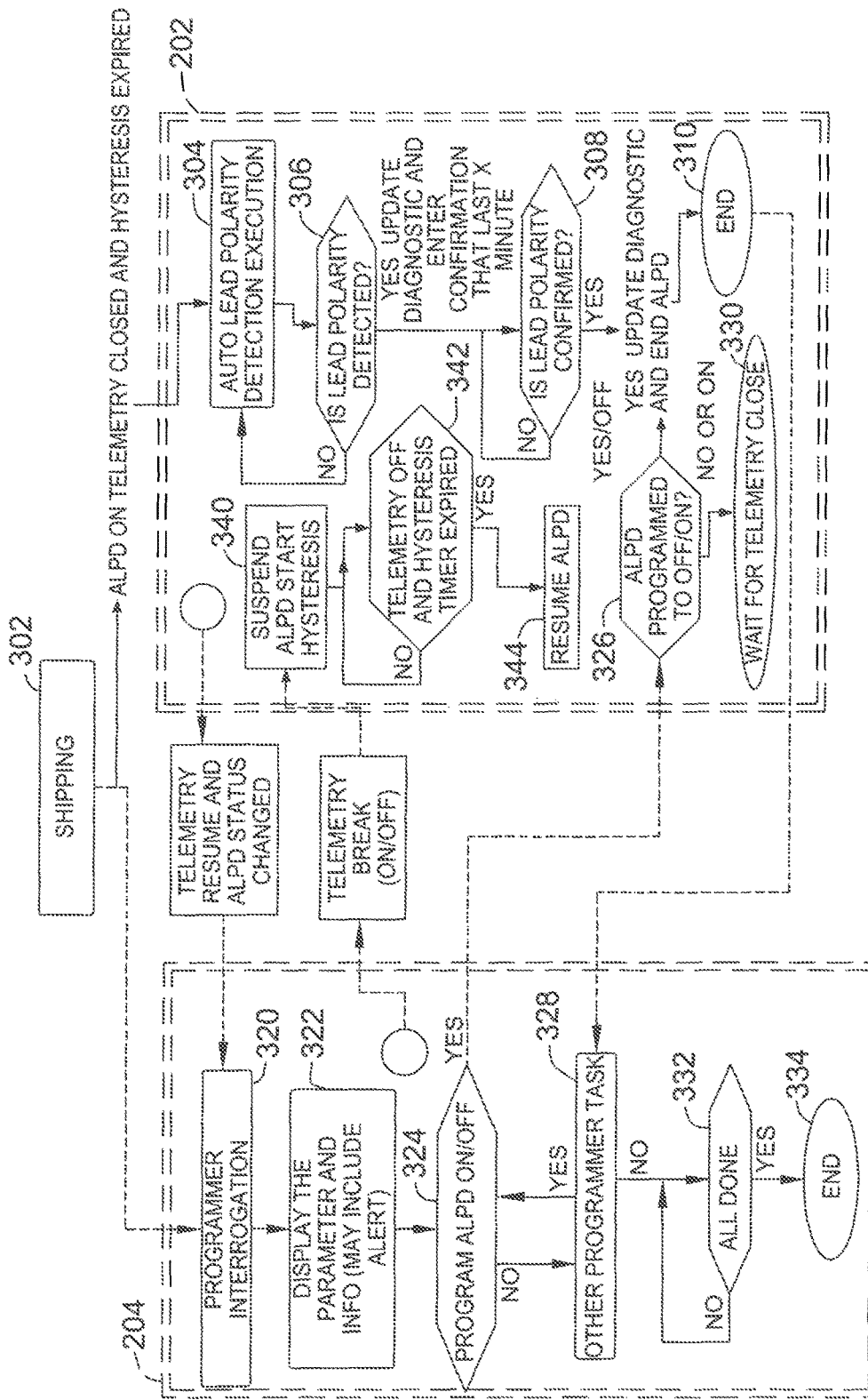
FIG. 3 is a detailed functional diagram of the ALPD system shown in FIG. 2.

FIG. 3 is a detailed functional diagram of ALPD system 200. As shown in FIG. 3, in this embodiment, upon shipping device 202 at block 302, the ALPD algorithm is enabled, telemetry (i.e., communication between device 202 and programmer 204) is disabled, and a hysteresis timer (described in more detail below) is expired. At block 304, device 202 initiates and executes the ALPD algorithm. At block 306, if a lead polarity is detected, a confirmation phase is entered, and flow proceeds to block 308. If a lead polarity is not detected, flow returns to block 304. At block 308, if lead polarity is confirmed (e.g., after a predetermined period of time), flow continues to block 310 and the ALPD algorithm ends. Otherwise, flow remains at block 308.

When telemetry is initiated between device 202 and programmer 204 (e.g., once a status of the ALPD algorithm changes), programmer interrogation occurs at block 320, and parameters and information determined by the ALPD algorithm are displayed (e.g., via an alert) on programmer 204 at block 322. Flow continues to block 324, where it is determined whether a user has chosen to deactivate or reactivate the ALPD algorithm. If the user has chosen to deactivate or reactivate the ALPD algorithm, flow continues to block 326. Otherwise, flow proceeds to block 328. At block 326, if the user has chosen to deactivate the ALPD algorithm, flow continues to block 310. If the user has chosen to reactivate the ALPD algorithm, flow continues to block 330, where device 202 waits for the telemetry to end.

At block 328, it is determined whether there is another task for programmer 204 to complete. If so, flow returns to block 324. If not, flow continues to block 332, where it is determined whether programmer 204 is done performing actions. If so, flow proceeds to block 334, and the process ends. If not, flow remains at block 332.

If telemetry breaks (i.e., fails) between device 202 and programmer 404, while at block 340, operation of the ALPD algorithm is suspended, and the hysteresis timer is started. Flow continues to block 342, where the flow remains until the hysteresis timer expires. Once the hysteresis timer expires, flow continues to block 344, and the ALPD algorithm resumes operation.

The ALPD algorithm, when executed by device 202, automatically detects whether device 202 is implanted and automatically determines the lead type, as described herein. More specifically, the ALPD algorithm automatically determines the device 202 is implanted when a lead connection with tissue is established, based on an in-range lead impedance measurement. Once the lead type is determined, appropriate pace and sense configurations are determined by the ALPD algorithm to provide immediate support for the patient's cardiac rhythm. When an external instrument (e.g., programmer 204) programs the lead type, or pace and sense configurations, the external instrument causes device 202 to disable the ALPD algorithm.

Figure 4:
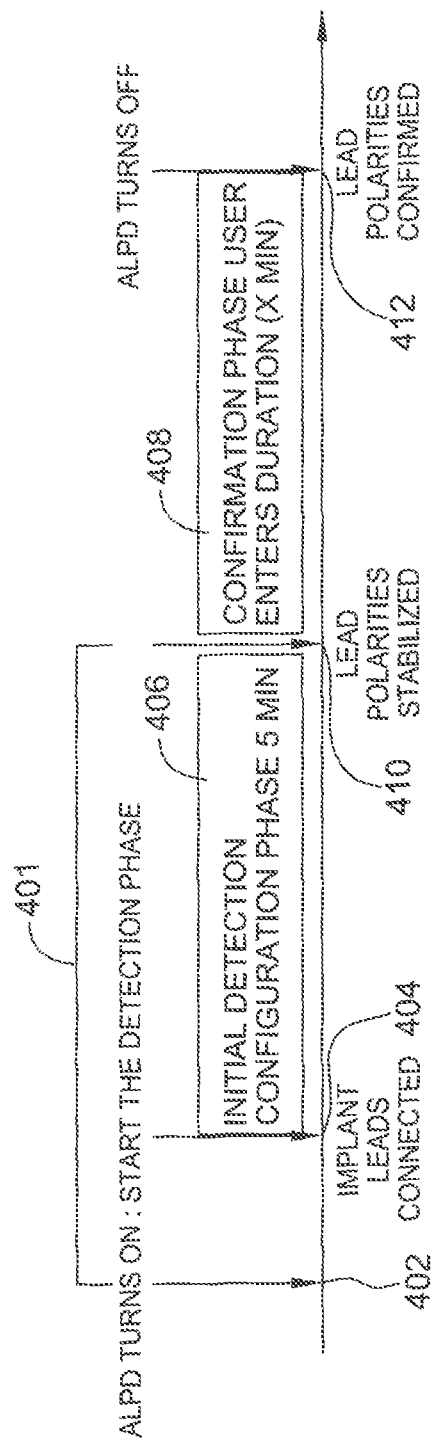
FIG. 4 is a diagram illustrating operation of one embodiment of an ALPD algorithm that may be used with the system shown in FIGS. 2 and 3.

FIG. 4 is a diagram illustrating operation of one embodiment of the ALPD algorithm, as executed by device 202. As shown in FIG. 4, the ALPD algorithm is activated and a detection phase 401 is initiated at a first time 402. At a second time 404, the ALPD algorithm detects that one or more implant leads have been connected to device 202, and an initial detection configuration phase 406 of the detection phase 401 begins. Initial detection configuration phase 406 lasts a predetermined settable time (e.g., approximately five minutes) until it is presumed lead polarities are stabilized. Initial detection configuration phase 406 ends and a confirmation phase 408 begins at a third time 410. The length of confirmation phase 408 may be specified by a user or be predetermined by the system. Confirmation phase 408 ends at a fourth time 412, at which the lead polarity configurations are finalized and the ALPD algorithm ends.

During detection phase 401, lead impedance measurement may be set such that the measurement can be completed within a cycle when a pacing rate is sixty pulses per minute (ppm). During detection phase 401, in this embodiment, right ventricular (RV) unipolar lead impedance is continuously measured at every third cycle to detect whether a RV unipolar or RV bipolar lead is implanted. A device with a RV bipolar lead placed in the patient's chest pocket will yield both an in-range bipolar lead measurement and an in-range unipolar lead measurement. In contrast, a RV unipolar lead in the patient's chest pocket will only yield an in-range unipolar lead impedance measurement. The measurement of RV unipolar lead impedance at every few cycles (e.g., three cycles in this embodiment) facilitates minimizing an impact to device longevity during shelf life, while still allowing for relatively quick RV lead implant detection. That is, with this design, RV lead implant will be detected within three seconds. Once detection phase 401 begins, the measurement sequence for four consecutive cycles is as follows: RV unipolar, no measurement (i.e., wait one second), no measurement (i.e., wait one second), and back to the beginning (i.e., RV unipolar again). This repeats until the RV unipolar measurement detects a RV unipolar connection.

Once an RV unipolar connection is detected, the algorithm transitions into initial detection configuration phase 406, which is still part of detection phase 401. Initial detection configuration phase 406 lasts for a predetermined settable time (e.g., five minutes) while it determines whether the lead connection is changed, which in turn causes the pace and sense configurations to be adjusted accordingly. The predetermined time is monitored using a detection timer. If the RV lead configuration changes, the detection timer is canceled, and the algorithm starts over again to search for the indication of another RV lead connection. The measurement sequence, in this embodiment, for the initial detection configuration phase 406 is as follows when an in-range RV unipolar measurement is detected by and in-range RV bipolar measurement is not detected: RV bipolar, RV unipolar, atrial bipolar, RV bipolar, RV unipolar, atrial unipolar, back to the beginning (i.e., RV bipolar again).

During initial detection configuration phase 406, the bipolar and unipolar lead impedances of the right ventricular and atrial chambers are measured to detect when leads are connected or changed. In this embodiment, the ALPD algorithm favors detection of the lead connection for the right ventricular chamber over the atrial chamber by alternating atrial bipolar and atrial unipolar measurements. After a physician tightens a screw and places device 202 in a patient's pocket for a bipolar lead, the algorithm detects an in-range unipolar lead impedance measurement. Therefore, the algorithm continually performs a bipolar measurement even if an in-range unipolar measurement is detected. On the other hand, if an in-range bipolar measurement is detected, the algorithm will skip the unipolar measurement. Specifically, in this embodiment, the measurement sequence for the initial detection configuration phase 406 is as follows when an in-range RV bipolar measurement is detected: RV bipolar, atrial bipolar, RV bipolar, atrial unipolar, back to the beginning (i.e., RV bipolar again). Once the detection timer expires, the lead polarity connection is considered stable, and the algorithm enters confirmation phase 408.

Figure 5A:
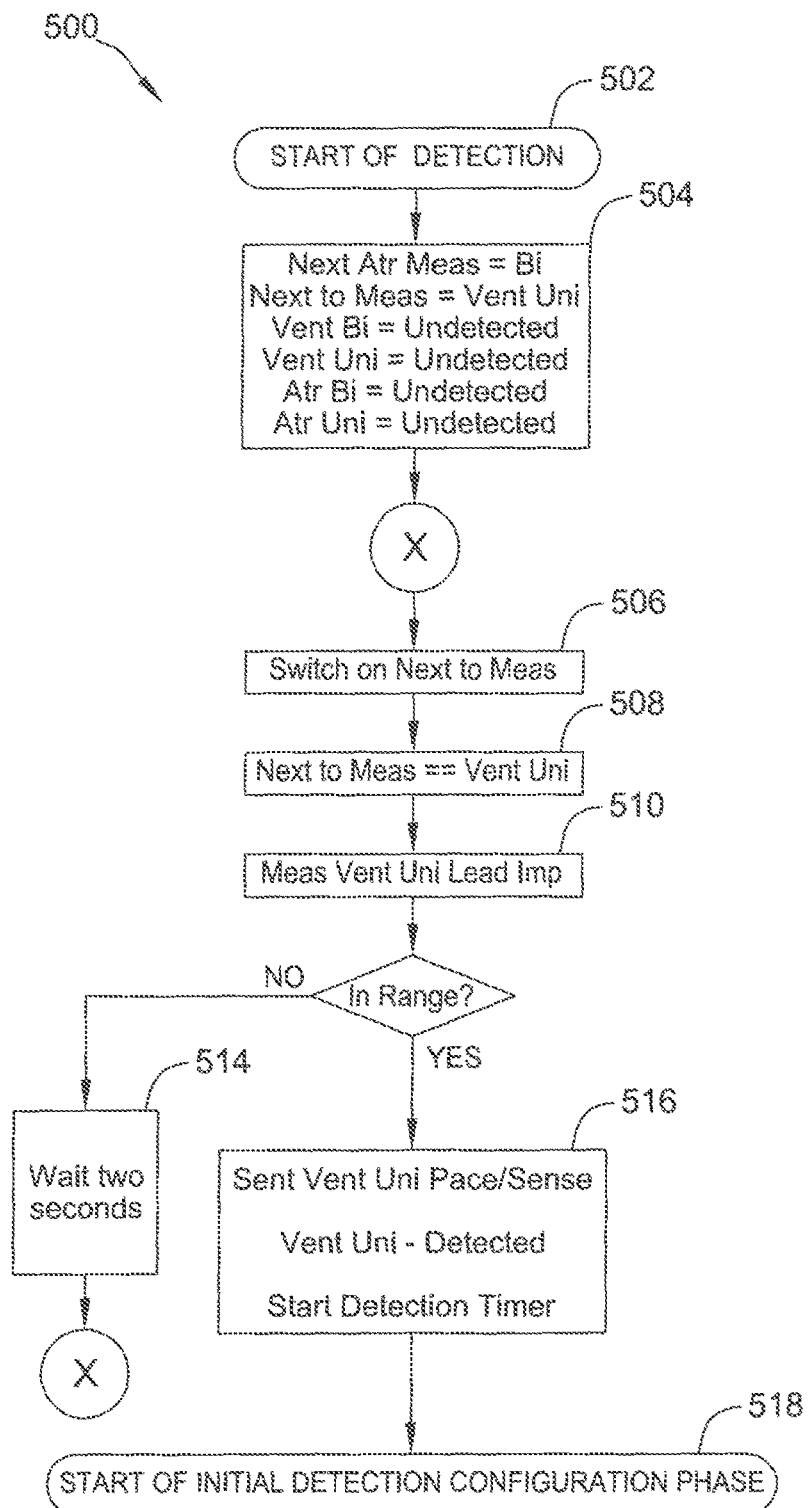
FIGS. 5A-5C are flow diagrams of an example method used in a detection phase of the ALPD algorithm.
Figure 5B:
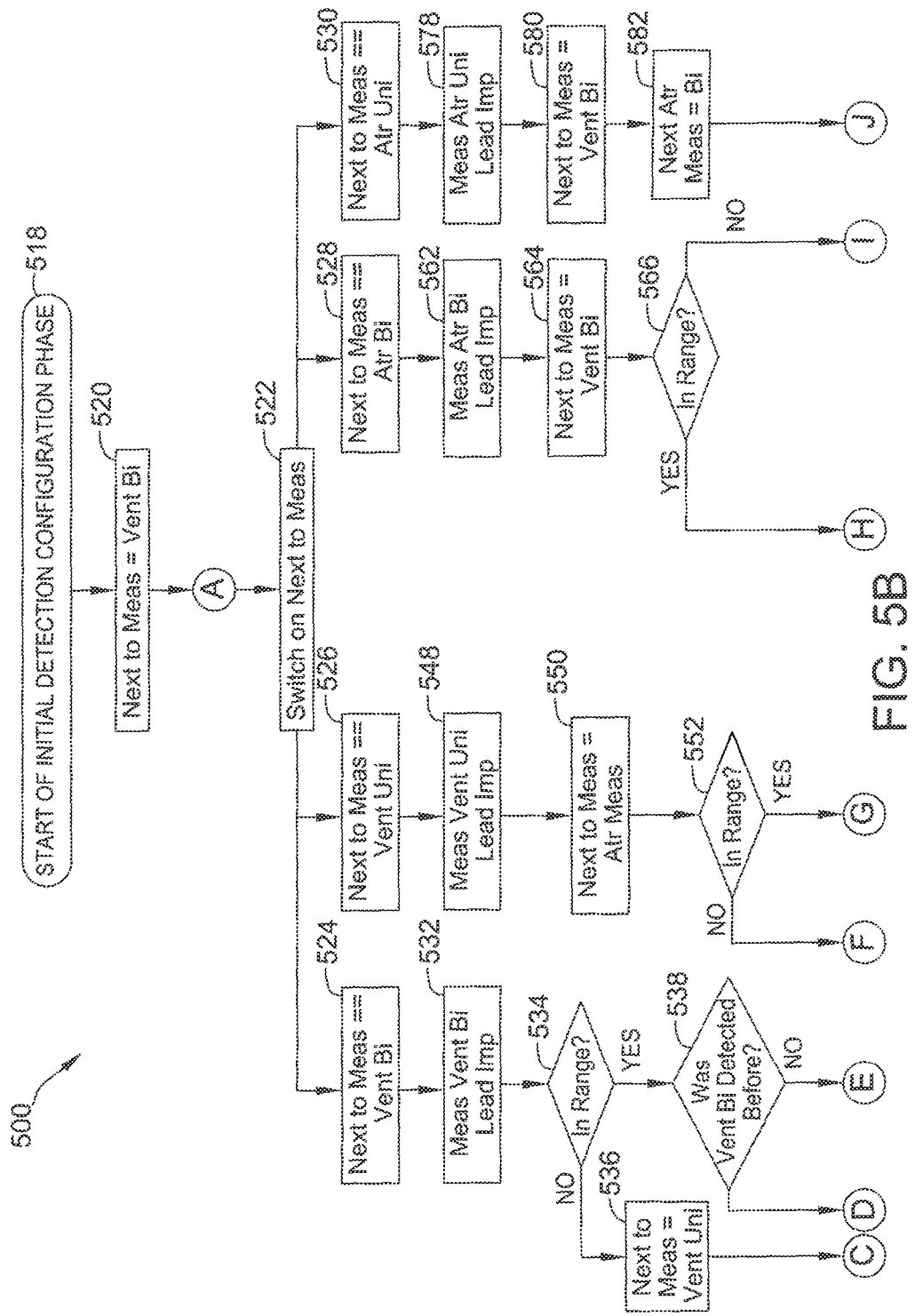
Figure 5C:
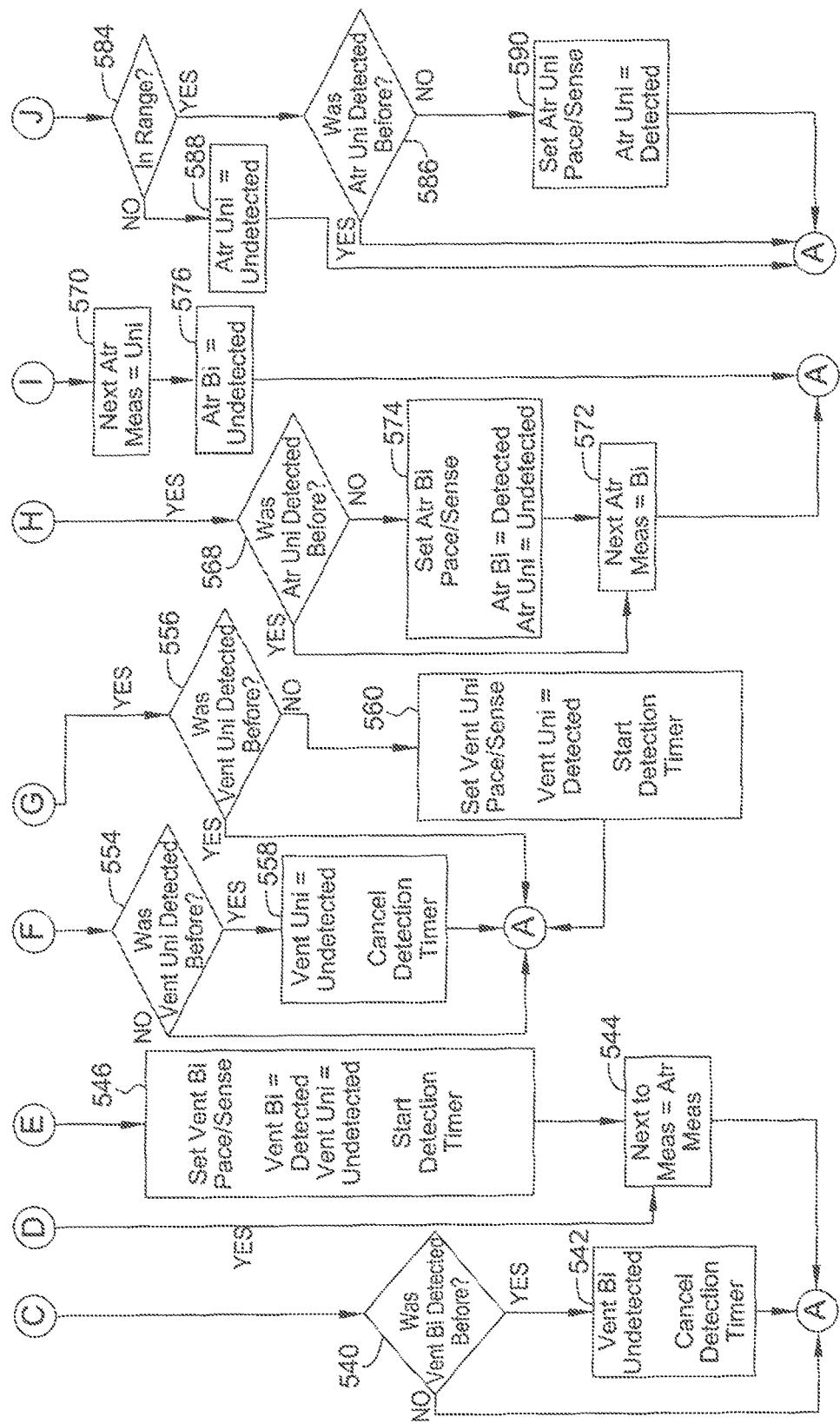

FIGS. 5A-5C are flow diagrams of an example method 500 utilized for detection phase 401 (including initial detection configuration phase 406). Detection phase 401 begins at block 502. At block 504, a next atrial measurement value is set to bipolar, a next to measure value is set to RV unipolar, and RV bipolar, RV unipolar, atrial bipolar, and atrial unipolar values are all set to undetected.

Flow proceeds to block 506, where the algorithm switches on the next to measure value. Since the next to measure value is set to RV unipolar, flow proceeds to block 508, and at block 510, the RV unipolar lead impedance is measured. At block 512, it is determined whether the RV unipolar lead impedance measurement is in range (e.g., below a predetermined threshold). If the RV unipolar lead impedance measurement is not in range, flow proceeds to block 514, which causes the algorithm to wait for two seconds (i.e., two cycles), before returning to block 506. If the RV unipolar lead impedance measurement is in range, flow proceeds to block 516, where the pace and sense configuration is set to an RV unipolar pace and sense configuration, the RV unipolar value is set to detected, and the detection timer (e.g., a five minute timer) is started. Flow then proceeds to block 518, where initial detection configuration phase 406 is initiated.

Referring now to FIGS. 5B and 5C, a flow diagram for initial detection configuration phase 406 of method 500 is shown. Flow begins at block 518, and continues to block 520, where the next to measure value is set to RV bipolar. Flow continues to block 522, where the algorithm switches on the next to measure value.

If the next to measure value is set to RV bipolar, flow proceeds from block 524. If the next to measure value is set to RV unipolar, flow proceeds from block 526. If the next to measure value is set to atrial bipolar (i.e., the next to measure value is set to atrial, and the next atrial measurement value is set to bipolar), flow proceeds from block 528. If the next to measure value is set to atrial unipolar (i.e., the next to measure value is set to atrial, and the next atrial measurement value is set to unipolar), flow proceeds from block 530.

From block 524, flow proceeds to block 532, where the RV bipolar lead impedance is measured. At bock 534, it is determined whether the RV bipolar lead impedance measurement is in range (e.g., below a predetermined threshold). If the RV bipolar lead impedance measurement is not in range, flow proceeds to block 536, where the next to measure value is set to RV unipolar. If the RV bipolar lead impedance measurement is in range, flow proceeds to block 538.

From block 538, flow proceeds to block 540. At block 540, if the RV bipolar value was previously set to detected, flow proceeds to block 542, where the RV bipolar value is set to undetected, and the detection timer is canceled, before returning to a point in method 500 just prior to block 522. In contrast, if the RV bipolar value was not previously set to detected, flow returns to a point in method 500 just prior to block 522.

At block 538, if the RV bipolar value was previously set to detected, flow proceeds to block 544, where the next to measure value is set to atrial, and the flow returns to a point in method 500 just prior to block 522. At block 538, if the RV bipolar value was not previously set to detected, flow proceeds to block 546, where the pace and sense configuration is set to an RV bipolar pace and sense configuration, the RB bipolar value is set to detected, the RV unipolar value is set to undetected, and the detection timer is started (if not already running). Flow proceeds from block 546 to block 544.

From block 526, flow proceeds to block 548, where the RV unipolar lead impedance is measured, and block 550, where the next to measure value is set to atrial. At block 552, it is determined whether the RV unipolar lead impedance measurement is in range. If the RV unipolar lead impedance measurement is not in range, flow proceeds to block 554. If the RV unipolar lead impedance measurement is in range, flow proceeds to block 556.

At block 554, if the RV unipolar value was not previously set to detected, the flow returns to a point in method 500 just prior to block 522. If the RV unipolar value was previously set to detected, the flow proceeds to block 558, where the RV unipolar value is set to detected and the detection timer is canceled, before flow returns to a point in method 500 just prior to block 522.

At block 556, if the RV unipolar value was previously set to detected, flow returns to a point in method 500 just prior to block 522. If the RV unipolar value was not previously set to detected, flow proceeds to block 560, where the pace and sense configuration is set to an RV unipolar pace and sense configuration, the RB unipolar value is set to detected, and the detection timer is started (if not already running). From block 560, flow proceeds to a point in method 500 just prior to block 522.

From block 528, flow proceeds to block 562, where the atrial bipolar lead impedance is measured, and block 564, where the next to measure value is set to RV bipolar. At block 566, it is determined whether the atrial bipolar lead impedance measurement is in range. If the atrial bipolar lead impedance measurement is in range, flow proceeds to block 568. If the atrial bipolar lead impedance measurement is not in range, flow proceeds to block 570.

At block 568, if the atrial bipolar value was previously set to detected, the flow continues to block 572, where the next atrial measurement value is set to bipolar, before the flow returns to a point in method 500 just prior to block 522. If the atrial bipolar value was not previously set to detected, the flow proceeds to block 574, where the pace and sense configuration is set to an atrial bipolar pace and sense configuration, the atrial bipolar value is set to detected, and the atrial unipolar value is set to undetected. From block 574, flow proceeds to block 572. At block 570, the next atrial measurement value is set to unipolar, and at block 576, the atrial bipolar value is set to undetected, before the flow returns to a point in method 500 just prior to block 522.

From block 530, flow proceeds to block 578, where the atrial unipolar lead impedance is measured, block 580, where the next to measure value is set to RV bipolar, and block 582, where the next atrial measurement is set to bipolar. At block 584, it is determined whether the atrial unipolar lead impedance measurement is in range. If the atrial unipolar lead impedance measurement is in range, flow proceeds to block 586. If the atrial unipolar lead impedance measurement is not in range, flow proceeds to block 588.

At block 586, if the atrial unipolar value was previously set to detected, flow returns to a point in method 500 just prior to block 522. If the atrial unipolar value was not previously set to detected, flow proceeds to block 590, where the pace and sense configuration is set to an atrial unipolar pace and sense configuration, and the atrial unipolar value is set to detected, before the flow returns to a point in method 500 just prior to block 522. At block 588, the atrial unipolar value is set to undetected, before the flow returns to a point in method 500 just prior to block 522.

As described above, the algorithm continues to operate in accordance with method 500 until the detection timer expires (i.e., the predetermined time is reached). At this point, the algorithm enters confirmation phase 408 (shown in FIG. 4).

In this embodiment, the duration of confirmation phase 408 is controlled by a programmable parameter (e.g., a user-specified length of time). For example, confirmation phase 408 may last for approximately twenty five minutes. During confirmation phase 408, the algorithm attempts to confirm that the lead connection type detected during detection phase 401 is correct. The algorithm continues to perform RV and atrial lead impedance measurements, but at a lead impedance measurement speed that uses two cycles (i.e., two seconds) to take one measurement. If a different RV lead type is detected during confirmation phase 408, the algorithm performs several retries to confirm this result before aborting confirmation phase 408 and returning to detection phase 401. At the end of confirmation phase 408, if no changes to lead type are detected, the algorithm terminates. The algorithm also programs atrial and RV trend configuration parameters for monitoring daily lead impedance measurements.

Notably, once the algorithm enters confirmation phase 408, it has detected either a RV unipolar or RB bipolar lead, but may not have necessarily detected an atrial lead type. Accordingly, during confirmation phase 408, the algorithm continuously monitors for an atrial lead connection and updates atrial pace and sense configurations accordingly.

In confirmation phase 408, the same situation as above applies where a bipolar lead measurement is needed even when the lead detected is unipolar. In this embodiment, the sequence of measurement in confirmation phase 408 when an RV unipolar lead is detected and no atrial lead is detected is as follows: RV unipolar, RV bipolar, atrial bipolar, atrial unipolar, back to beginning (i.e., RV unipolar again).

RV unipolar is measured first because it is detected. RV bipolar is measured to recheck that lead. Atrial bipolar and unipolar are measured to check for an atrial lead connection. In this embodiment, the sequence of measurement in confirmation phase 408 when an RV bipolar lead is detected and an atrial unipolar lead is detected is as follows: RV bipolar, atrial unipolar, atrial bipolar, back to beginning (i.e., RB bipolar again). RV bipolar is measured because it is detected. Atrial unipolar is measured before atrial bipolar because it is detected, and atrial bipolar is detected to recheck on that lead.

Figure 6A:
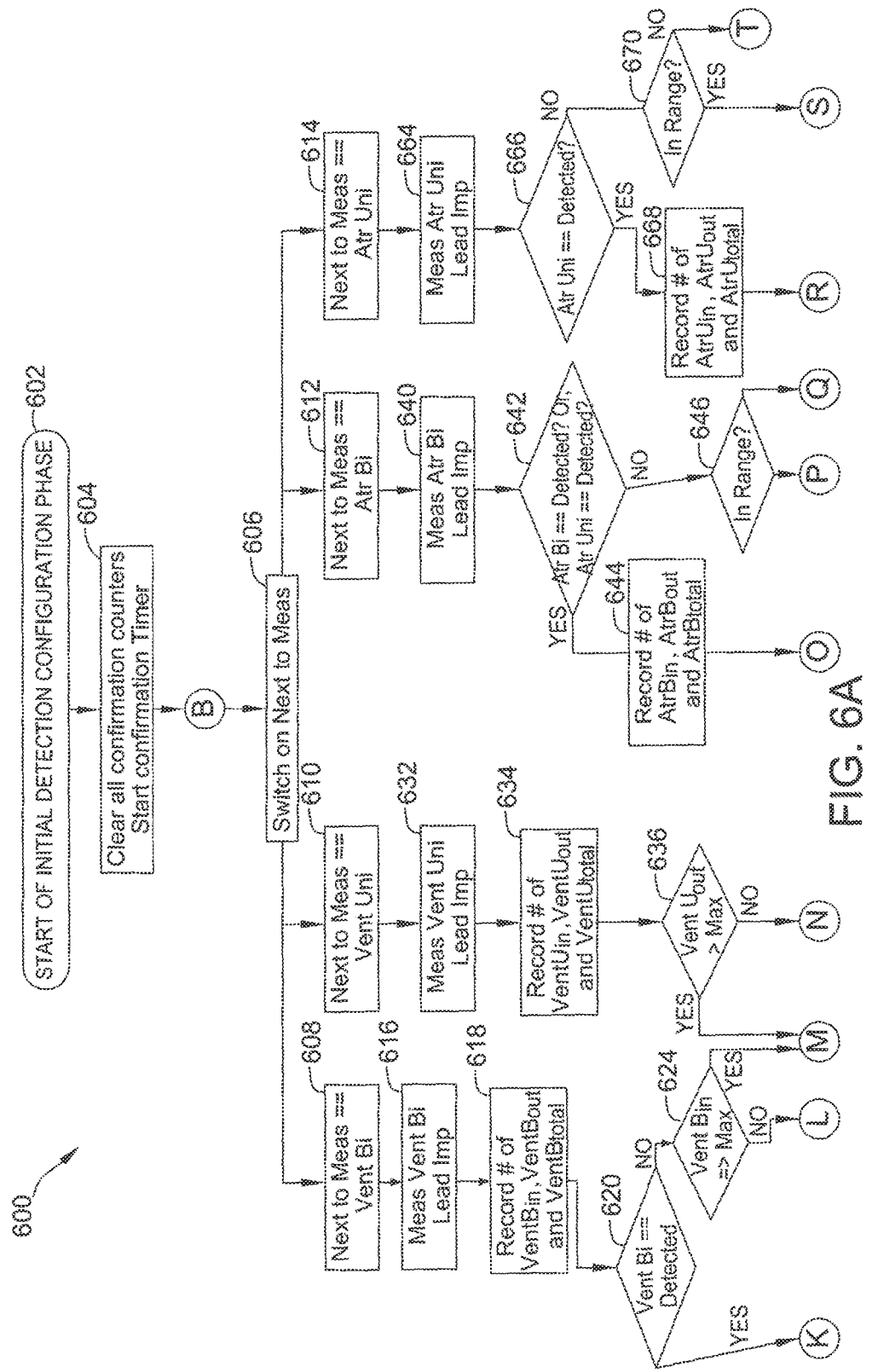
FIGS. 6A and 6B are a flow diagram of an example method used In a confirmation phase of the ALPD algorithm.
Figure 6B:
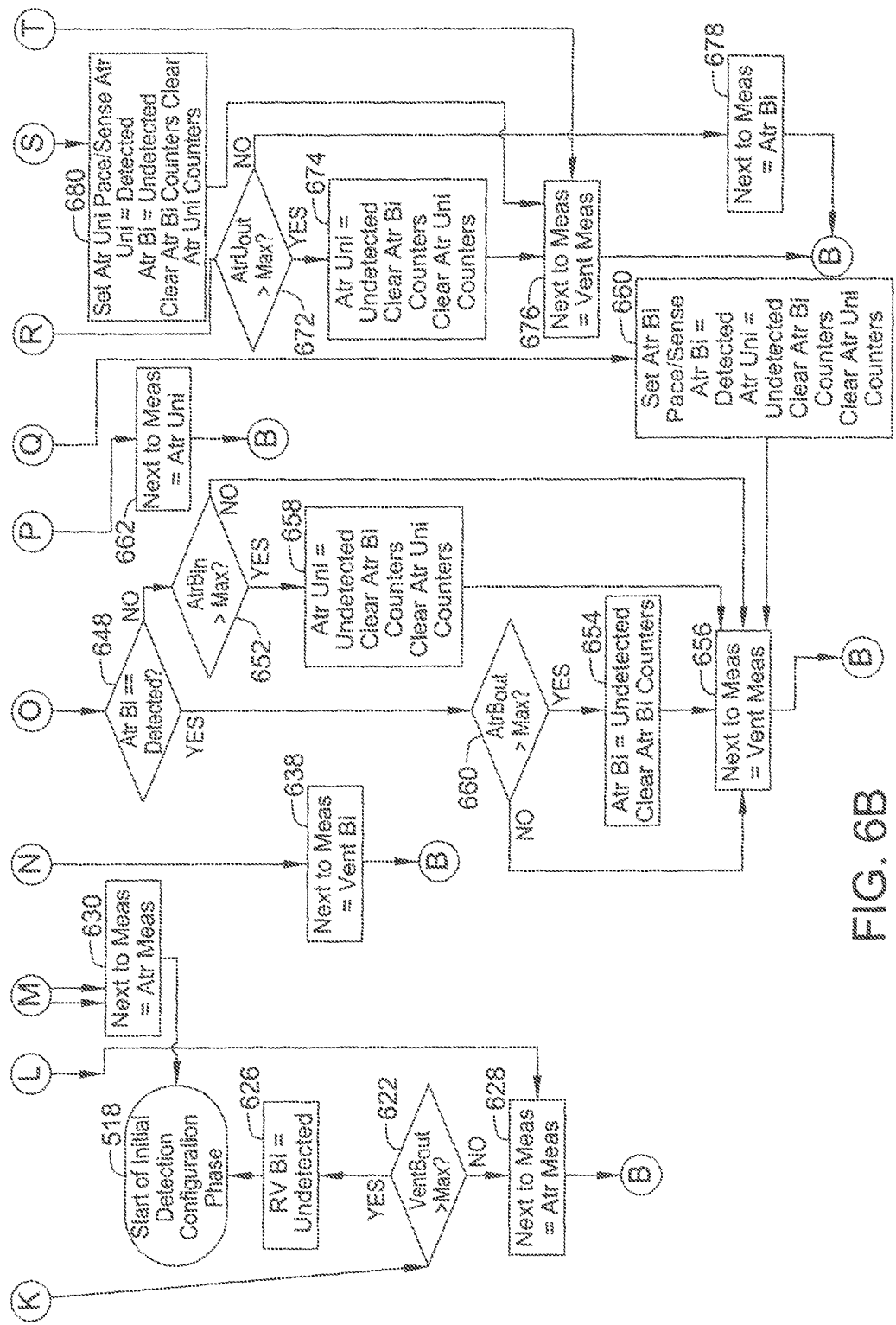

FIGS. 6A and 6B are a flow diagram of an example method 600 utilized for confirmation phase 408. Confirmation phase 408 begins at block 602. At block 604, all confirmation counters are cleared, and a confirmation timer (e.g., for the user-specified length of time) is started. Flow continues to block 606, where the algorithm switches on the next to measure value.

If the next to measure value is set to RV bipolar, flow proceeds from block 608. If the next to measure value is set to RV unipolar, flow proceeds from block 610. If the next to measure value is set to atrial bipolar (i.e., the next to measure value is set to atrial, and the next atrial measurement value is set to bipolar), flow proceeds from block 612. If the next to measure value is set to atrial unipolar (i.e., the next to measure value is set to atrial, and the next atrial measurement value is set to unipolar), flow proceeds from block 614.

From block 608, flow proceeds to block 616, where the RV bipolar lead impedance is measured. At block 618, a current number of RV bipolar lead impedance measurements in range (VentB$_{in}$), a current number of RV bipolar lead impedance measurements not in range (VentB$_{out}$), and a total number of RV bipolar lead impedance measurements (VentB$_{total}$) are recorded (e.g., on memory 194). At block 620, if the RV bipolar value is set to detected flow proceeds to block 622. If the RV bipolar value is set to undetected flow proceeds to block 624.

At block 622, if VentB$_{out}$ is greater than a predetermined threshold (e.g., 10), the RV bipolar measurement is set to undetected at block 626, and the flow returns to block 518. If VentB$_{out}$ is not greater than a predetermined threshold, the next to measure value is set to atrial at block 628, and flow returns to just prior to block 606.

At block 624, if VentB$_{in}$ is greater than a predetermined threshold, the RV unipolar value is set to undetected at block 630, and the flow returns to block 518. If VentB$_{in}$ is not greater than a predetermined threshold, flow proceeds to block 628.

From block 610, flow proceeds to block 632, where the RV unipolar lead impedance is measured. At block 634, a current number of RV unipolar lead impedance measurements in range (VentU$_{in}$), a current number of RV unipolar lead impedance measurements not in range (VentU$_{out}$), and a total number of RV unipolar lead impedance measurements (VentU$_{total}$) are recorded (e.g., on memory 194).

At block 636, if VentU$_{out}$ is greater than a predetermined threshold, flow proceeds to block 630. If not, flow proceeds to block 638, where the next to measure value is set to RV bipolar, before flow returns to just prior to block 606.

From block 612, flow proceeds to block 640, where the atrial bipolar lead impedance is measured. At block 642, if the atrial bipolar value is set to detected or the atrial unipolar value is set to detected, flow proceeds to block 644. Otherwise, flow proceeds to block 646.

At block 644, a current number of atrial bipolar lead impedance measurements in range (AtrB$_{in}$), a current number of atrial bipolar lead impedance measurements not in range (AtrB$_{out}$), and a total number of atrial bipolar lead impedance measurements (AtrB$_{total}$) are recorded (e.g., on memory 194). At block 648, it the atrial bipolar value is set to detected, flow proceeds to block 650. If not, flow proceeds to block 652.

At block 650, if AtrB$_{out}$ is greater than a predetermined threshold (e.g., 10), the atrial bipolar measure is set to undetected and the atrial bipolar counters (AtrB$_{in}$, AtrB$_{out}$, and AtrB$_{total}$) are cleared at block 654, and the next to measure value is sent to RV at block 656, before the flow returns to just prior to block 606. If AtrB$_{out}$ is not greater than a predetermined threshold, flow proceeds directly to block 656.

At block 652, if AtrB$_{in}$ is greater than a predetermined threshold, the atrial unipolar value is set to undetected, the atrial unipolar counters are cleared, and the atrial bipolar counters are cleared at block 658, before flow proceeds to block 656. If AtrB$_{in}$ is not greater than a predetermined threshold, flow proceeds directly to block 656.

At block 646, if the atrial bipolar lead impedance measurement is in range, flow proceeds to block 660, where the pace and sense configuration is set to an atrial bipolar pace and sense configuration, the atrial bipolar value is set to detected, the atrial unipolar value is set to undetected, the atrial unipolar counters are cleared, and the atrial bipolar counters, all before flow proceeds to block 656. If the atrial bipolar lead impedance measurement is not in range, flow proceeds to block 662, where the next to measure value is set to atrial unipolar, before the flow returns to just prior to block 606.

From block 614, flow proceeds to block 664, where the atrial unipolar lead impedance is measured. At block 666, if the atrial bipolar value is set to detected flow proceeds to block 668. Otherwise, flow proceeds to block 670.

At block 668, a current number of atrial unipolar lead impedance measurements in range (AtrU$_{in}$), a current number of atrial unipolar lead impedance measurements not in range (AtrU$_{out}$), and a total number of atrial unipolar lead impedance measurements (AtrU$_{total}$) are recorded (e.g., on memory 194).

At block 672, if AtrU$_{out}$ is greater than a predetermined threshold, the atrial unipolar value is set to undetected, the atrial unipolar counters are cleared, and the atrial bipolar counters are cleared at block 674, before flow proceeds to block 676. At block 676, the next to measure value is set to RV, before the flow returns to a point just prior to block 606. If, at block 672, AtrB$_{in}$ is not greater than a predetermined threshold, flow proceeds to block 678, where the next to measure value is set to atrial bipolar, before the flow returns to a point just prior to block 606.

At block 670, if the atrial unipolar lead impedance measurement is in range, flow proceeds to block 680, where the pace and sense configuration is set to an atrial unipolar pace and sense configuration, the atrial bipolar value is set to undetected, the atrial unipolar value is set to detected, the atrial unipolar counters are cleared, and the atrial bipolar counters, all before flow proceeds to block 676. If the atrial unipolar lead impedance measurement is not in range, flow proceeds to block 676.

As explained above, the algorithm continues to operate in accordance with method 600 until the confirmation timer expires. At this point, in this embodiment, the algorithm ends.

In this embodiment, the ALPD algorithm may be suspended when a logical channel is open, to prevent interaction with user input. When the logical channel closes, a hysteresis timer is started, and the ALPD algorithm resumes when the hysteresis timer expires and if there is no user input to determine the configuration. The purpose of the hysteresis timer is to prevent a transient telemetry break from causing the ALPD algorithm to suspend and resume constantly. If the logical channel re-opens before the hysteresis timer expires, the timer is canceled.

The particular lead configuration measurement that was suspended will be resumed when the ALPD algorithm resumes. If the ALPD detection timer or confirmation timer is running, the associated timer is paused when the logical channel opens, and resumes when the ALPD resumes. There are at least two reasons to suspend the ALPD algorithm during an external instrument session. First, the physician may be running tests that interfere with impedance measurements. Second, it is desirable to prevent race conditions that are caused by the external device manipulating the pace and sense configurations what are the same parameters controlled by the ALPD algorithm.

Figure 7:
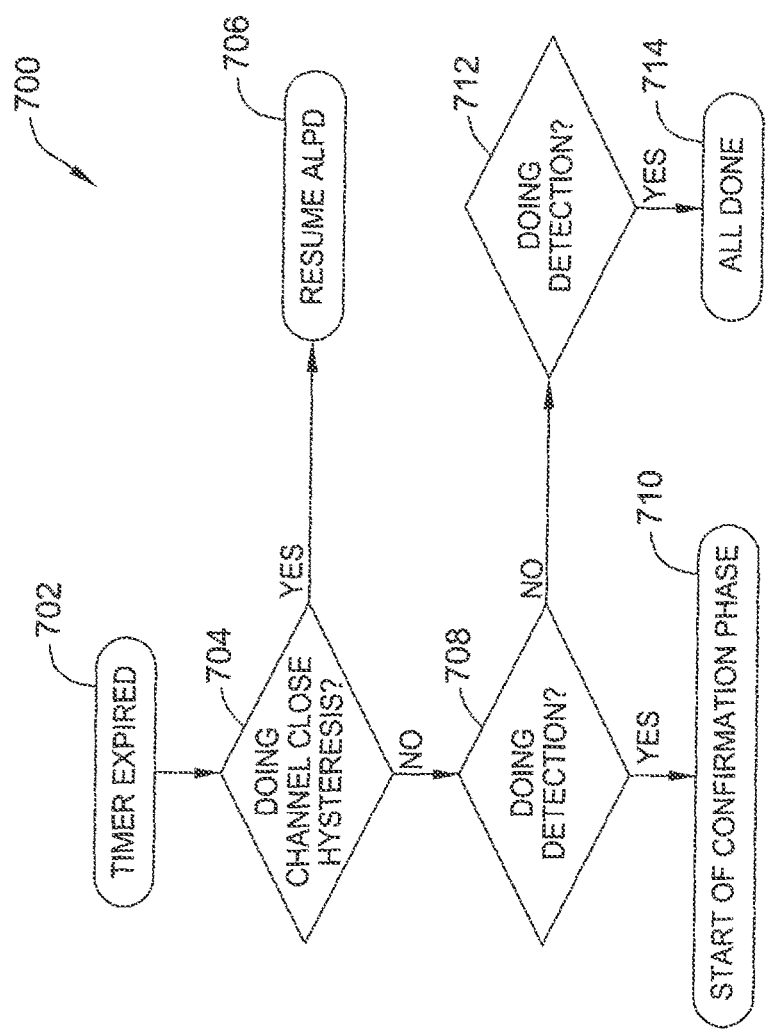
FIG. 7 is a flow diagram of an example method for managing timer expiration in the ALPD algorithm.

FIG. 7 is a flow diagram illustrating a method 700 for managing the various timer (e.g., hysteresis, detection, confirmation) expirations. One of the timers expires at block 702. From block 704, if the timer is the hysteresis timer, the ALPD algorithm is resumed at block 706. If the timer is not the hysteresis timer, flow proceeds to block 708.

At block 708, if the timer is the detection timer, the confirmation phase begins at block 710. If the timer is not the detection timer, flow proceeds to block 712. At block 712, if the timer is the confirmation timer, the ALPD algorithm ends at block 714.

The systems and methods described herein facilitate automatically detecting pace and sense configurations for an implantable cardiac device. By monitoring impedance measurements, a pace and sense configuration is detected and confirmed by the implantable cardiac device. The pace and sense configuration may be automatically transmitted to a programmer device.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An implantable cardiac device comprising:
   at least one lead having one or more electrodes configured in a unipolar, bi-polar or multi-polar configuration to perform unipolar, bi-polar or multi-polar pacing and sensing operations;
   an impedance sensor configured to measure lead impedance for a plurality of electrode configurations;
   a memory; and
   a controller communicatively coupled to the memory and configured to:
      automatically detect the implantation of the at least one lead and connection of the at least one lead to the implanted cardiac device based on one more lead impedance measurements acquired using the impedance sensor;
      automatically determine, during a detection phase, a lead electrode configuration based on a plurality of first lead impedance measurements using the impedance sensor and automatically determine a pace and sense electrode configuration for the at least one lead based upon the electrode configuration; and
      confirm, during a confirmation phase, the electrode configuration and the pace and sense configuration based on a plurality of second lead impedance measurements acquired using the impedance sensor.

2. The implantable cardiac device of claim 1, wherein the pace and sense configuration includes at least one of a right ventricular unipolar pace and sense configuration, a right ventricular bipolar pace and sense configuration, an atrial unipolar pace and sense configuration, and an atrial bipolar pace and sense configuration.

3. The implantable cardiac device of claim 1, wherein the controller is configured to end the detection phase and begin the confirmation phase after a predetermined period of time has elapsed.

4. The implantable cardiac device of claim 3, wherein the predetermined period of time is approximately five minutes.

5. The implantable cardiac device of claim 1, wherein the controller is configured to end the confirmation phase and operate the implantable cardiac device in accordance with the finalized pace and sense configuration after a predetermined period of time has elapsed.

6. The implantable cardiac device of claim 5, wherein the predetermined period of time is specified by a user operating a programmer that is communicatively coupled to the implantable cardiac device.

7. The implantable cardiac device of claim 1, wherein the controller is configured to automatically transmit the pace and sense configuration to a programmer that is communicatively coupled to the implantable cardiac device.

8. A system comprising:
   an implantable cardiac device comprising:
      at least one lead having one or more electrodes configured in a unipolar, bi-polar or multi-polar configuration to perform unipolar, bi-polar or multi-polar pacing and sensing operations;
      an impedance sensor configured to measure lead impedance for a plurality of electrode configurations;
      a memory; and
      a controller communicatively coupled to the memory and configured to:
         automatically detect the implantation of the at least one lead and connection of the at least one lead to the implanted cardiac device based on one more lead impedance measurements acquired using the impedance sensor;
         automatically determine, during a detection phase, a lead electrode configuration based on a plurality of first lead impedance measurements acquired using the impedance sensor and automatically determine a pace and sense configuration for the at least one lead based upon the electrode configuration; and
         confirm, during a confirmation phase, the electrode configuration and the pace and sense configuration based on a plurality of second lead impedance measurements acquired using the impedance sensor; and
   a programmer communicatively coupled to the implantable cardiac device.

9. The system of claim 8, wherein the pace and sense configuration includes at least one of a right ventricular unipolar pace and sense configuration, a right ventricular bipolar pace and sense configuration, an atrial unipolar pace and sense configuration, and an atrial bipolar pace and sense configuration.

10. The system of claim 8, wherein the controller is configured to end the detection phase and begin the confirmation phase after a predetermined period of time has elapsed.

11. The system of claim 10, wherein the predetermined period of time is approximately five minutes.

12. The system of claim 8, wherein the controller is configured to end the confirmation phase and operate the implantable cardiac device in accordance with the pace and sense configuration after a predetermined period of time has elapsed.

13. The system of claim 12, wherein the predetermined period of time is specified by a user operating the programmer.

14. The system of claim 8, wherein the controller is configured to automatically transmit the pace and sense configuration to the programmer.

15. A method of operating an implantable cardiac device, the method comprising:
- automatically detecting the implantation of a lead and connection of the lead to the implanted cardiac device based on one more lead impedance measurements;
- automatically determining, during a detection phase, a unipolar, bipolar or multi-polar lead electrode configuration based on a plurality of first lead impedance measurements using a first electrode configuration and automatically determining a pace and sense configuration for the lead based upon the electrode configuration;
- restarting detection or confirming, during a confirmation phase, the electrode configuration and the pace and sense configuration based on a plurality of second lead impedance measurements using a first electrode configuration; and
- operating the implantable cardiac device in accordance with the pace and sense configuration.

16. The method of claim 15, wherein automatically determining a pace and sense configuration includes automatically determining at least one of a right ventricular unipolar pace and sense configuration, a right ventricular bipolar pace and sense configuration, an atrial unipolar pace and sense configuration, and an atrial bipolar pace and sense configuration.

17. The method of claim 15, further comprising ending the detection phase and beginning the confirmation phase after a predetermined period of time has elapsed.

18. The method of claim 15, further comprising ending the confirmation phase and operating the implantable cardiac device in accordance with the pace and sense configuration after a predetermined period of time has elapsed.

19. The method of claim 18, further comprising receiving, at the implantable cardiac device, data specifying the predetermined period of time from a programmer.

20. The method of claim 15, further comprising automatically transmitting the pace and sense configuration to a programmer.

* * * * *